(12) United States Patent
Elbert et al.

(10) Patent No.: US 6,322,538 B1
(45) Date of Patent: Nov. 27, 2001

(54) GASTRO-INTESTINAL TUBE PLACEMENT DEVICE

(75) Inventors: Linda D. Elbert, Bloomington, IN (US); D. H. Perkins, Woods Cross, UT (US); Srinivas Nishtala, Bloomington, IN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/252,407

(22) Filed: Feb. 18, 1999

(51) Int. Cl.[7] ..................................................... A61M 5/32
(52) U.S. Cl. ...................... 604/174; 604/105; 604/164.03
(58) Field of Search .................................... 604/104, 105, 604/106, 107, 108, 158, 164.01, 164.03, 164.04, 174, 96

(56) References Cited

U.S. PATENT DOCUMENTS

| 4,861,334 | 8/1989 | Nawaz . | |
|---|---|---|---|
| 4,900,306 | 2/1990 | Quinn et al. . | |
| 5,080,650 | 1/1992 | Hirsch et al. . | |
| 5,112,310 | * 5/1992 | Grobe | 604/175 |
| 5,356,391 | * 10/1994 | Stewart | 604/175 |
| 5,376,094 | * 12/1994 | Kline | 606/113 |

* cited by examiner

Primary Examiner—Richard K. Seidel
Assistant Examiner—Jennifer Maynard
(74) Attorney, Agent, or Firm—Kenyon & Kenyon

(57) ABSTRACT

A gastro-intestinal tube placement device for percutaneously placing gastro-intestinal tubes into the gastric cavity. The gastro-intestinal tube placement device of the present invention includes a containment element, such as an overtube, through which a gastro-intestinal tube can pass, and a displacing element assembly for pushing a gastro-intestinal tube through the containment element. The present invention also includes a gastro-intestinal tube having a collapsible internal bolster at its distal end, which bolster is capable of being manipulated to have a reduced lateral extent that allows the tube to be placed within the containment element.

3 Claims, 5 Drawing Sheets

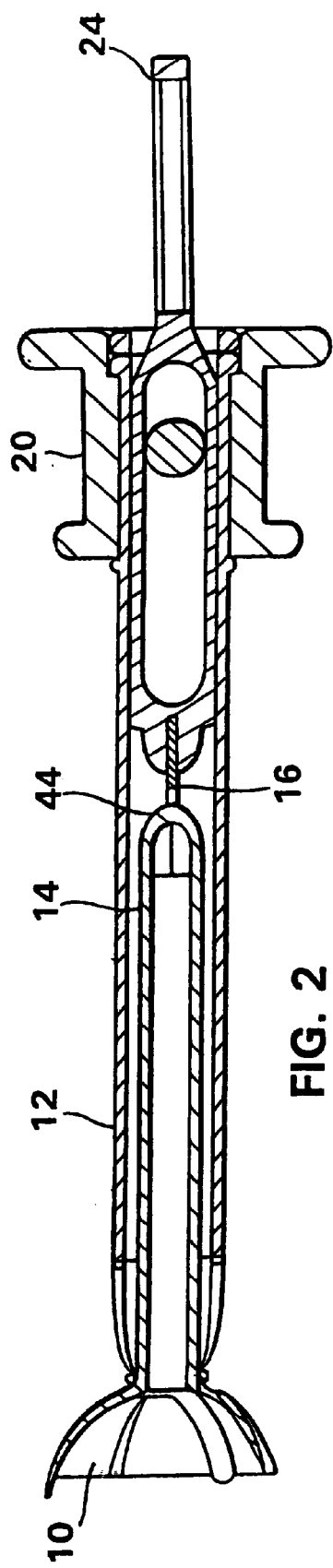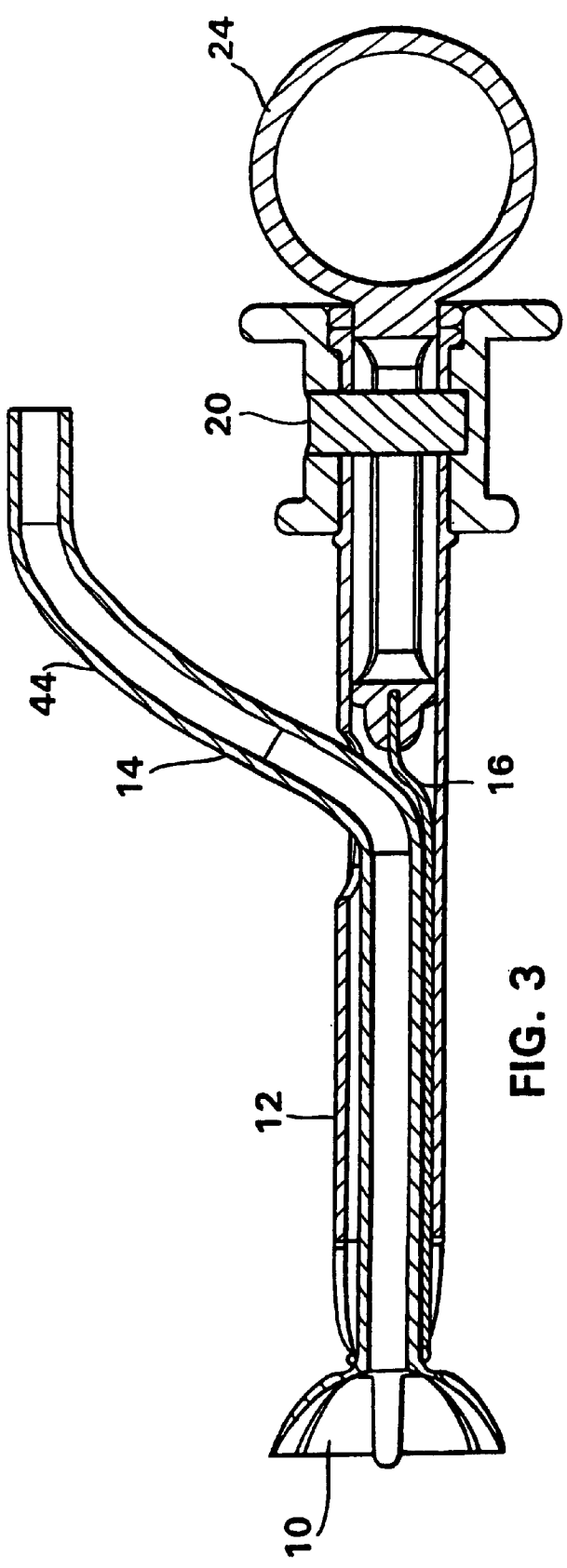

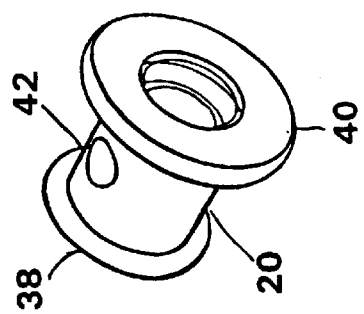
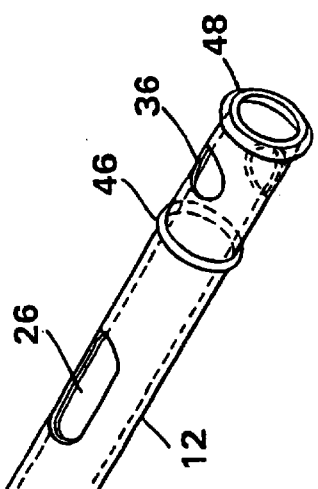
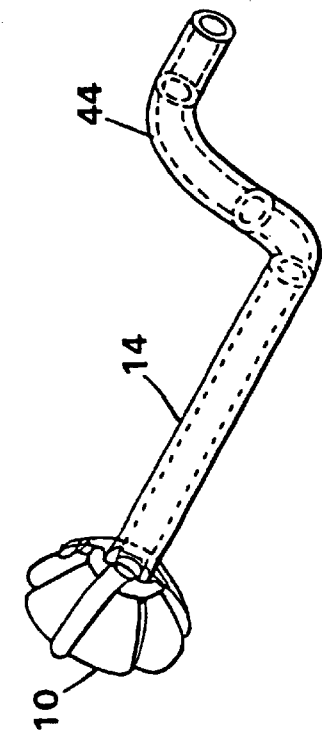
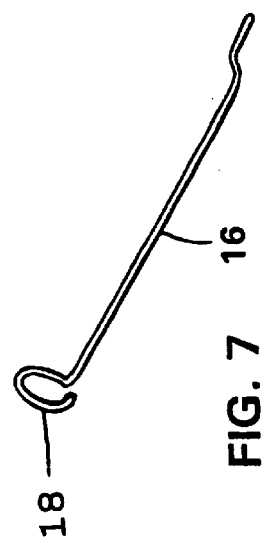
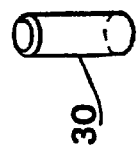

GASTRO-INTESTINAL TUBE PLACEMENT DEVICE

FIELD OF THE INVENTION

The present invention relates generally to an apparatus for use in the placement of gastro-intestinal devices. More specifically, the present invention relates to a gastro-intestinal tube placement device which includes a tube deployment apparatus and a gastro-intestinal tube with a collapsible internal bolster.

BACKGROUND OF THE INVENTION

Medical practitioners utilize a variety of gastro-intestinal devices to access the gastro-intestinal tract. One type of gastro-intestinal device, the gastro-intestinal tube or gastrostomy tube, is widely used with patients who require catheterization for the purposes of, for example, delivering food or medication to the gastro-intestinal tract, draining the tract, or creating a surgical port.

Medical practitioners often use Percutaneous Endoscopic Gastrostomy (PEG) techniques, such as those described in U.S. Pat. Nos. 4,861,334; 4,900,306; and 5,080,650, to place tubes within the gastro-intestinal tract. These techniques typically involve either placing a gastro-intestinal tube in the patient's mouth and snaking it down the esophagus, into the stomach, and out the abdominal wall, or they involve inserting a tube into the stomach from outside of the abdominal wall by sliding the tube over a guidewire.

Gastro-intestinal tubes are often equipped with internal bolsters, or anchoring devices, at one end which help prevent the tube from being prematurely or inadvertently pulled through the stoma or other tract through which it has been placed. While serving that purpose, the size, shape and rigidity of these bolsters often frustrate attempts to place tubes equipped with such bolsters using PEG techniques.

When the tube is properly placed, the internal bolster lies inside the stomach wall, and the tube shaft extends out through the abdominal wall. Thus, when using PEG placement techniques which entail snaking the tube into place, the internal bolster is dragged along with the tube through the gastro-intestinal tract, often causing tissue trauma and potential contamination of the tract. Further, internal bolsters are often too large and rigid to allow placement by threading a bolster-equipped tube through a tract over a guidewire.

The internal bolsters also make tube removal difficult. Because the bolsters are often too large and rigid to allow easy removal by, for example, traction pull from outside the stomach, tubes with internal bolsters are often removed with an endoscopic snare.

SUMMARY OF THE INVENTION

The present invention provides a gastro-intestinal placement device which permits placement, through an existing stoma, of a gastro-intestinal tube with an internal bolster. The invention includes a gastro-intestinal tube with a collapsible internal bolster and a tube deployment device.

In the preferred embodiment, the deployment device has a containment element, such as an overtube, with an expandable distal tip and a slot through which the shaft of a gastro-intestinal tube can be threaded. The deployment device can be preloaded with the gastro-intestinal tube to form the placement device. The tube is loaded into the deployment device by collapsing or otherwise reducing the lateral extent of the tube's bolster, placing the bolster inside of the overtube at the overtube's distal end, and threading the shaft of the gastro-intestinal tube out through the slit in the overtube.

In that embodiment, the deployment device also has a displacing element, such as a pushtube, which is used to force the bolster out of the distal end of the overtube. In addition, the deployment device has a thumb-ring attached to the pushtube which facilitates moving the pushtube distally during tube placement. The deployment tube also has a spool at the proximal end of the overtube which provides physicians with a base on which to place their fingers and steady the deployment device during tube placement. The gastro-intestinal tube preferably has a collapsible bolster of umbrella-like design with retention ribs connected by cross-webbing. The bolster is preferably formed with memory of the umbrella-like shape.

BRIEF DESCRIPTION OF THE DRAWINGS

The invention will be more readily understood through the following detailed description, with reference to the accompanying drawings, in which:

FIG. 2 is a top cross-sectional view of an embodiment of the present invention, showing a gastro-intestinal tube placed partially within a gastro-intestinal tube deployment device, in which the collapsible bolster is shown in its expanded state protruding out from the distal end of the tube.

FIG. 3 is an elevational cross-sectional side view of the present invention, showing a gastro-intestinal tube placed partially within a gastro-intestinal tube deployment device, in which the collapsible bolster is shown in its expanded state protruding out from the distal end of the tube.

FIG. 4 is a perspective view of a gastro-intestinal tube of the present invention.

FIG. 5 is a perspective view of an overtube component of a gastro-intestinal tube deployment device according to the present invention.

FIG. 6 is a perspective view of a spool component of a gastro-intestinal tube deployment device according to the present invention.

FIG. 7 is a perspective view of a pusher component of a gastro-intestinal tube deployment device according to the present invention.

FIG. 8 is a perspective view of a plug component of a gastro-intestinal tube deployment device according to the present invention.

DETAILED DESCRIPTION OF THE INVENTION

Figure 1:
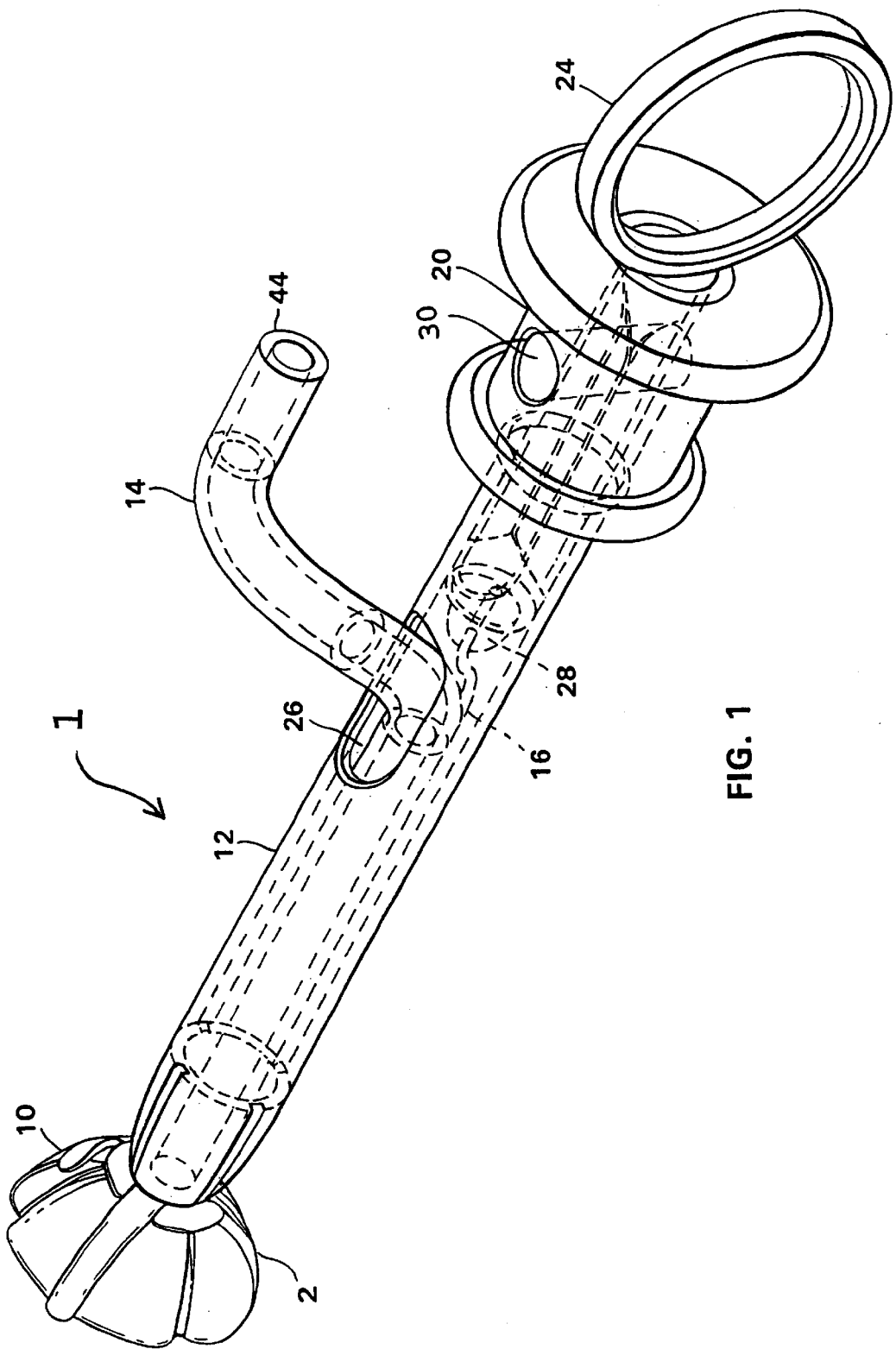
FIG. 1 is a perspective view, partially in section, of the preferred embodiment of the present invention, showing a gastro-intestinal tube placed partially within a gastro-intestinal tube deployment device, which tube has a collapsible bolster at its distal end that has been deployed.

The preferred embodiment of the gastro-intestinal tube deployment device 1 of the present invention is shown in FIG. 1. That device is made of several components: a gastro-intestinal tube 14, a pusher assembly 28, a spool 20, and a plug 30. Each of those components is shown separately in FIGS. 4–8, respectively. FIG. 1 shows the assembled gastro-intestinal tube deployment device 1 of the present invention.

The assembled placement device 1 allows a physician to place a gastro-intestinal tube which has a collapsible internal bolster easier than if the physician used prior art methods and devices. During the deployment procedure, the placement device 1 is inserted through a path through which the gastro-intestinal tract can be reached. The path can be created by, for example, a stoma, a surgical port or a cannula. Any path which allows passage of the placement device 1 from outside of a patient's body to any location within the gastro-intestinal tract will suffice. For ease of discussion, however, reference will hereinafter be made to a path to the stomach via stoma.

Prior to tube placement, the physician can snake an endoscope into the patient's stomach so that the insertion site can be viewed during placement. The physician can then see the point at which the placement device 1 is properly inserted through the stoma. Once the placement device 1 is properly inserted, the pusher 16 is moved distally to push the collapsible bolster 10 past the distal end 2 of the placement device 1. Once so pushed, the bolster 10 deploys to its extended state, as shown in FIG. 1. The deployment device 1 can then be pulled from the stoma.

As the device 1 is pulled proximally, the deployed bolster 10 serves as an anchor inside the stomach wall, preventing the tube 14 from being pulled out through the stoma. During removal of device 1, the portion of shaft 44 of the gastro-intestinal tube 14 which was threaded out through the opening 26 in the overtube 12, is pulled in through the opening 26 and out the distal end 2 of the device 1. Once the placement device 1 is removed, the gastro-intestinal tube 14 is left in place inside the stomach.

The spool 20 and the thumb-ring 24 facilitate tube placement by providing sites for the physician to place his fingers. During placement, the physician places two fingers on the spool 20, on opposite sides of the spool 20 between the distal ridge 38 and the proximal ridge 40, and places his thumb in the thumb-ring 24. The physician then uses his thumb to push distally on the thumb-ring 24, which is connected to the pusher 16.

FIG. 4 shows a gastro-intestinal tube 14 with a collapsible internal bolster 10 at its distal end and a tube shaft 44. The collapsible internal bolster 10 can be folded, deformed or otherwise reduced in lateral extent so as to allow the bolster 10 and the distal end of the tube 14 to be preloaded into the overtube 12. When loaded, the collapsible bolster 10 and a portion of the distal end of the tube shaft 44 lie within the overtube 12. The remaining length of the tube shaft 44 is threaded out of the overtube 12 through an opening 26, as shown in FIG. 1.

The overtube 12, shown in FIG. 5, is a tubular structure with an expandable distal end 50 and an opening 26. The central lumen of the overtube 12 is capable of housing the gastro-intestinal tube 14 being placed and the pusher 16. The overtube 12 serves as the conduit through which the gastro-intestinal tube is placed. During tube placement, the pusher 16 is moved distally, forcing the tube's bolster 10 out of the overtube's distal end.

The expandable distal tip 50 of the overtube 12 expands to facilitate passage of the tube bolster 10 out of the overtube. The overtube depicted in FIG. 5 has slits 52 which form petals 54. During deployment of the bolster (i.e. pushing the bolster 10 out of the distal end of the overtube 12) the petals 54 are forced outward and apart, allowing easy passage of the bolster out of the overtube 12.

Although the overtube 12 is preferably formed with slits 52, the overtube 12 need not be so formed. The distal tip 50 can be made expandable in many ways. For example, the distal tip 50 can be formed with overlapping folds or with a web structure having petals and flexible material between the petals. In addition, the overtube can be made without an expandable distal tip 50. Although the expandable tip 50 facilitates tube placement, the tube bolster 10 can be forced out of the distal end of an overtube that does not have such a tip.

As shown in FIG. 6, the spool 20 of the placement device 1 is a tube-like structure with a central lumen, a distal ridge 38 and a proximal ridge 40. The spool 20 fits over the overtube 12 at the proximal end of the device assembly 1. As shown in FIG. 5, the overtube 12 can have distal and proximal stops, 46 and 48 respectively, which hold the spool 20 in place. In addition, the overtube 12 and spool 20 can be held together by a plug 30, shown in FIG. 8. The plug 30 is placed through bore holes 36 in the overtube 12 and bore holes 42 in the spool. The plug 30 keeps the spool 20 from moving with respect to the overtube 12.

The pusher 16, shown in FIG. 7, is a rod which runs through the overtube 12, allowing the physician to push the bolster 10 out of the distal end of the overtube 12. The pusher 16 preferably has a ring 52 at its distal end which fits around the shaft 44 of the gastro-intestinal tube 14 at the base of the bolster 10. With the ring 52, the force of the distally-moving pusher 16 is applied to the circumference of the bolster's base. Alternatively, the pusher can be a straight rod. In addition, other components can be attached to the pusher rod 16, to form a pusher assembly (an example of which is shown in FIG. 1). The pusher assembly shown in FIG. 1 includes a thumb-ring attached to its proximal end.

FIGS. 2 and 3 show top cross-sectional and elevational cross-sectional side views, respectively, of the first embodiment of the gastro-intestinal tube placement device of the present invention.

Figure 9:
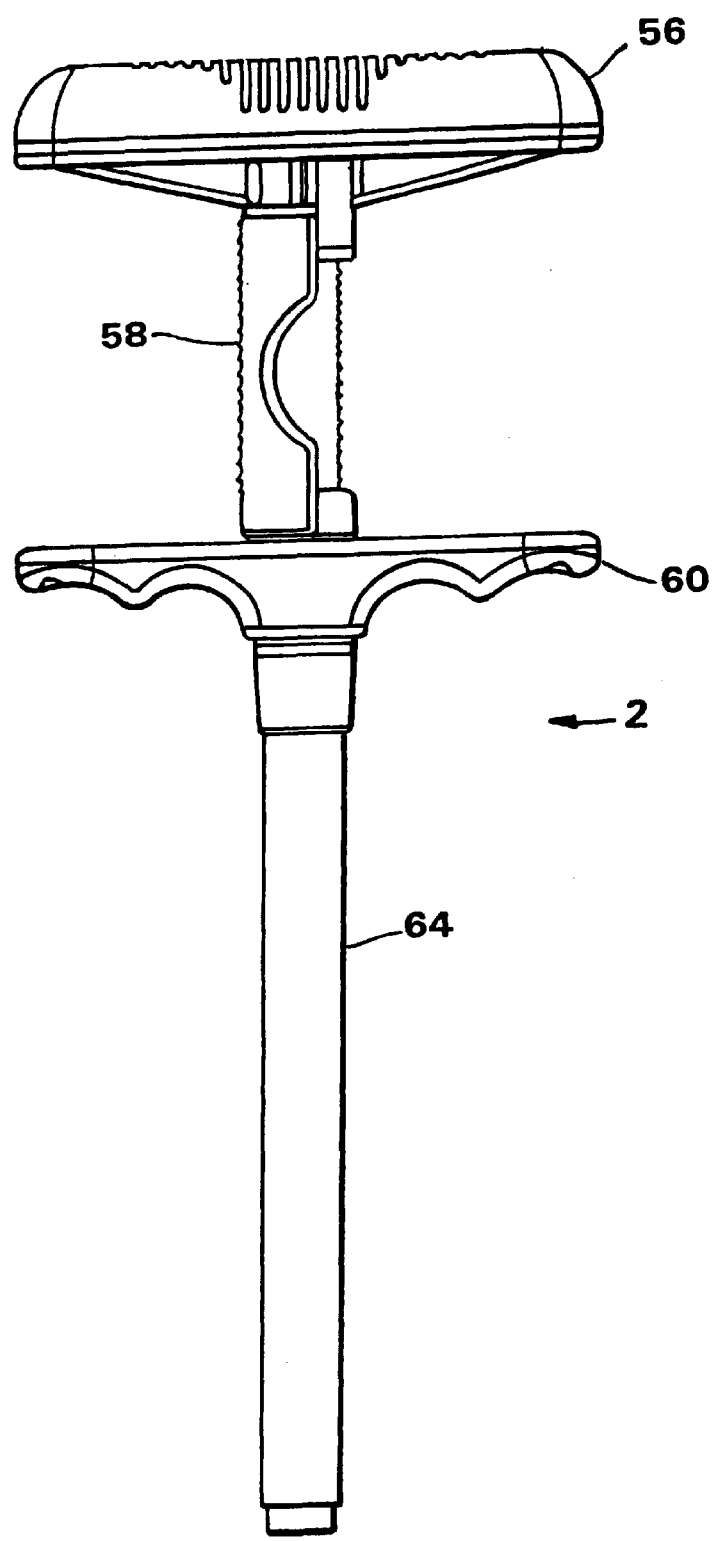
FIG. 9 is an elevational view of a second embodiment of a gastro-intestinal tube deployment device according to the present invention.

Another embodiment of the gastro-intestinal tube placement device 2 of the present invention is shown in FIG. 9. In that embodiment, the pusher is a rod which slides inside the overtube 64. The overtube finger flange 60 provides a base for the physician's fingers, much like the spool 20, of the previous embodiment. The push tube press 56 provides a base against which the physician can push during placement. The physician can push on the press 56 with either the thumb or the palm of his hand.

Figure 10:
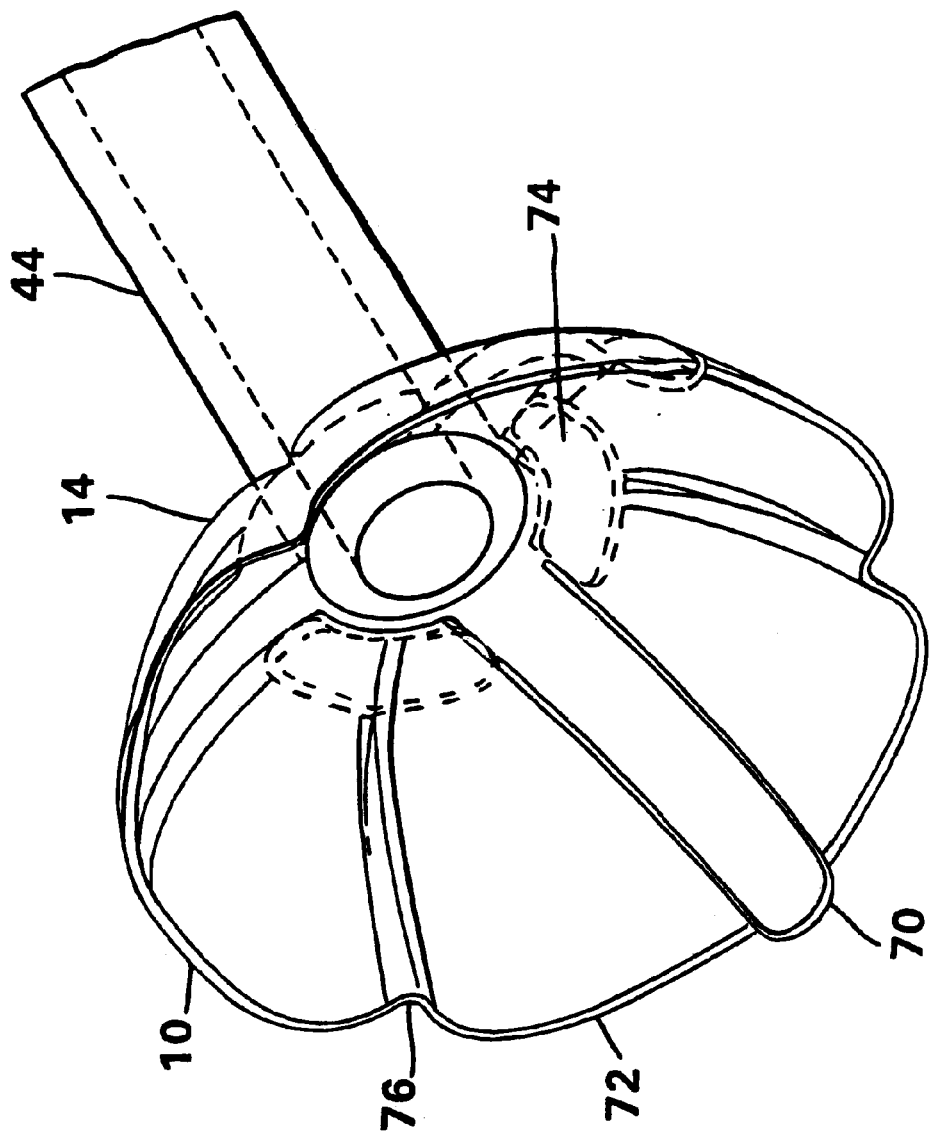
FIG. 10 is a perspective view of an internal bolster according to the present invention.

FIG. 10 shows a collapsible internal bolster 10 which is used with the device described above. Although it can be appreciated that any internal bolster may be used which can be collapsed, compressed or otherwise reduced in lateral extent to allow loading within the overtube, the embodiment shown in FIG. 10 is preferred.

The bolster 10 has an umbrella-like design in which retention ribs 70 are connected by cross-webbing 72. Both the ribs 70 and cross-webbing can be made of silicone copolymers or other plastic. The cross-webbing 72 is sufficiently thin that it folds when the ribs 70 are pushed distally and towards the longitudinal axis of the tube 14. The cross-webbing 72 is preferably formed with predetermined fold lines 76, and thinned areas 74 near the base of the bolster 10. The fold lines 76 and thinned areas 74 permit the cross-webbing 72 to fold in a predetermined manner.

The bolster 10 is preferably manufactured with memory for the umbrella-like shape (i.e. the shape that the bolster 10 will have in its un-compressed state inside the stomach). Thus, once bolster 10 is pushed past the distal end of the overtube 12, the bolster returns to its predetermined umbrella-like shape. In this predetermined shape, the bolster anchors the tube within the stomach. When more than a threshold amount of proximally-directed force is applied, however, the bolster will collapse, allowing removal by traction pull.

The bolster 10 is preferably made of a soft plastic that is capable of maintaining memory, such as silicone, a polyurethane or ethylene vinyl acetate. In addition, the bolster 10 is preferably about 1 inch in diameter and 1 inch from its distal-most point to its most proximal point. Those dimensions can change, however, depending on the plastic material utilized. When more rigid plastic material is used, the dimensions can be smaller. When a less rigid plastic material is used, the dimensions may need to be larger.

What is claimed is:

1. A gastro-intestinal tube placement device comprising:

a containment element having proximal and distal ends and a central lumen extending therethrough;

a displacing element assembly disposed within the central lumen of the containment element, substantially from the proximal end to the distal end of the containment element; and a spool disposed at the proximal end of the containment element, the spool including a tubular body with a proximal end and a distal end and including outwardly projecting ridges at the proximal end and the distal end of the tubular body, wherein the spool defines two aligned bore holes and wherein the containment element defines two aligned bore holes, the bore holes of the containment element aligned with the bore holes of the spool, and further comprising a plug disposed through the bore holes of the spool and the bore holes of the containment element.

2. A gastro-intestinal tube placement device comprising:

a containment element having proximal and distal ends and a central lumen extending therethrough;

a displacing element assembly disposed within the central lumen of the containment element, substantially from the proximal end to the distal end of the containment element; and a gastro-intestinal tube having a proximal end and a distal end, and a collapsible internal bolster at the distal end of the tube wherein a first portion of the tube is disposed inside the central lumen of the containment element such that the internal bolster lies at the distal end of the containment element, wherein the containment element defines an opening along a length through which a second portion of the tube is disposed.

3. A gastro-intestinal tube placement device comprising:

a containment element having a proximal end and a distal end and a central lumen extending therethrough, wherein the proximal end defines two aligned bore holes;

a displacing element assembly disposed within the central lumen of the containment element, substantially from the proximal end to the distal end of the containment element;

a spool disposed at the proximal end of the containment element, the spool including a tubular body with a proximal end and a distal end and including outwardly projecting ridges at the proximal end and the distal end of the tubular body, wherein the spool defines two aligned bore holes, the bore holes of the containment element aligned with the bore holes of the spool; and a plug disposed through the bore holes of the spool and the bore holes of the containment element.

* * * * *